United States Patent [19]

Dill, II

[11] Patent Number: 5,567,616
[45] Date of Patent: Oct. 22, 1996

[54] APPARATUS FOR SUPPORTING AND DRIVING A ROTATING CYLINDER

[75] Inventor: John J. Dill, II, Kalamazoo, Mich.

[73] Assignee: Dill Instruments, Kalamazoo, Mich.

[21] Appl. No.: 206,776

[22] Filed: Mar. 7, 1994

[51] Int. Cl.$^6$ .............................. C12M 1/10; C12M 1/42
[52] U.S. Cl. .................. 435/283.1; 435/2; 435/292.1; 422/24; 366/220; 366/233; 250/432 R; 250/436; 604/4
[58] Field of Search .................... 435/2, 173.1, 285, 435/289, 310, 311, 312, 316, 808, 283.1, 286.1, 286.2, 286.4, 286.5, 292.1, 298.2; 422/24, 209; 366/220, 233; 384/549, 565; 250/435, 432 R, 438, 435; 604/4

[56] References Cited

U.S. PATENT DOCUMENTS

| | | | |
|---|---|---|---|
| 551,196 | 12/1895 | Richards | 384/549 |
| 710,523 | 10/1902 | Schaad | 384/549 |
| 1,782,622 | 11/1930 | Kilian | 384/549 |
| 1,925,875 | 9/1933 | McLaughlin et al | 384/549 |
| 2,838,291 | 6/1958 | Peebles | 384/549 |
| 2,923,146 | 2/1960 | Mayer . | |
| 3,295,801 | 1/1967 | McDowall et al. | 384/549 |
| 3,351,309 | 11/1967 | Harrison . | |
| 3,356,324 | 12/1967 | Attermeyer . | |
| 3,485,576 | 12/1969 | McRae et al. | 422/24 |
| 3,592,423 | 7/1971 | Mui . | |
| 4,496,133 | 1/1985 | Sule . | |
| 4,524,802 | 6/1985 | Lawrence et al. . | |
| 4,626,241 | 12/1986 | Campbell et al. . | |
| 4,632,356 | 12/1986 | Munz . | |
| 4,635,897 | 1/1987 | Gallant . | |
| 4,684,102 | 8/1987 | Dykstra . | |
| 4,780,178 | 10/1988 | Yoshida et al. | 422/99 |
| 4,890,942 | 1/1990 | Raasch | 384/549 |
| 4,893,946 | 1/1990 | Tesh et al. | 384/549 |
| 4,904,874 | 2/1990 | Ellner | 250/436 |
| 5,133,932 | 7/1992 | Gunn et al. | 422/24 |
| 5,154,896 | 10/1992 | Mochida et al. | 422/209 |
| 5,368,399 | 11/1994 | Tremblay | 384/565 |

FOREIGN PATENT DOCUMENTS

| | | | |
|---|---|---|---|
| 3739966 | 6/1989 | Germany | 422/24 |
| 0810791 | 3/1959 | United Kingdom | 384/549 |

Primary Examiner—William Beisner
Attorney, Agent, or Firm—Robert C. Curfiss; Butler & Binion, L.L.P.

[57] ABSTRACT

An irradiator includes a support structure for supporting and rotating a cylinder of the type used for treating fluids. The cylinder is hollow and is mounted for rotation about an inclined axis for permitting fluids such as blood constituents to flow by gravity downward along the internal peripheral wall of the cylinder. The angle of inclination, the drive speed and the thickness of the fluid film on the wall of the cylinder are controlled and variable in order to achieve consistent and predictable results during various treatment processes, and for critical in controlling the precise exposure of the fluid to the lamp. A unique collection cup is provided at the discharge end of the cylinder for receiving the discharged, treated fluid and the collection cup is designed to receive and seat one end of the lamp assembly. The cylinder is mounted on roller bearings having a resilient bearing surface for isolating potential external vibration. A removable resilient ring is placed on the outer surface of the bearing to provide the isolating bearing surface. The resilient bearing configuration may also be used to support the cylinder on the selected angle of inclination. To further isolate the cylinder against vibration, the drive mechanism is mounted on a floating mount with a resilient, sound deadening drive belt extending around the outer perimeter of the cylinder. The base is mounted on levelers permitting independent leveling of each of the three or four legs without a tendency of the structure to walk.

22 Claims, 6 Drawing Sheets

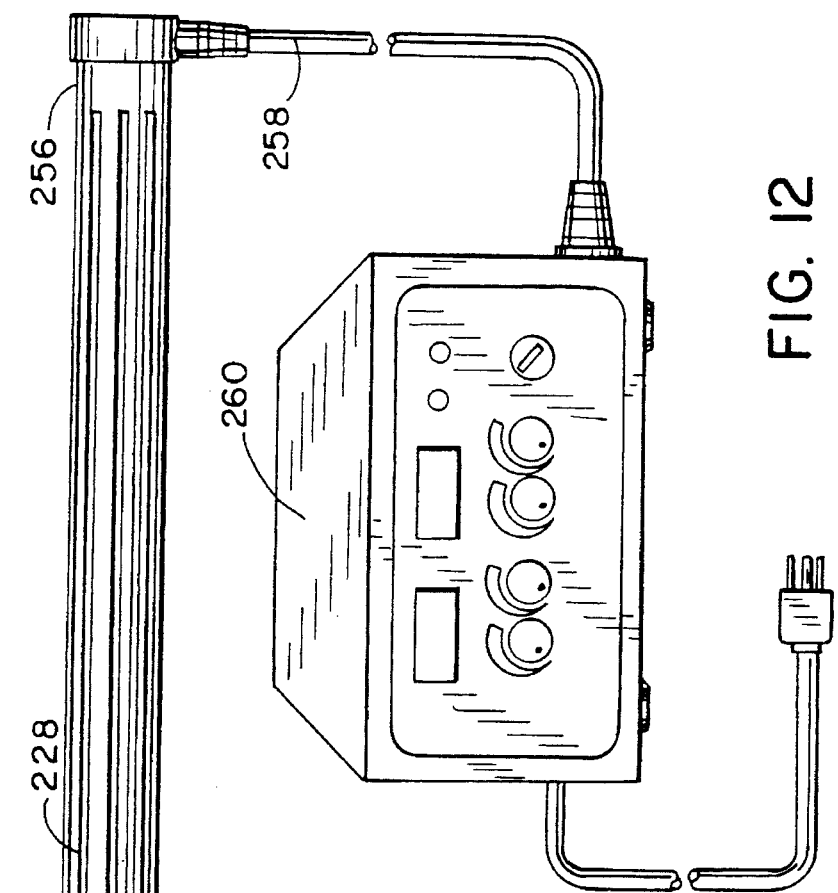
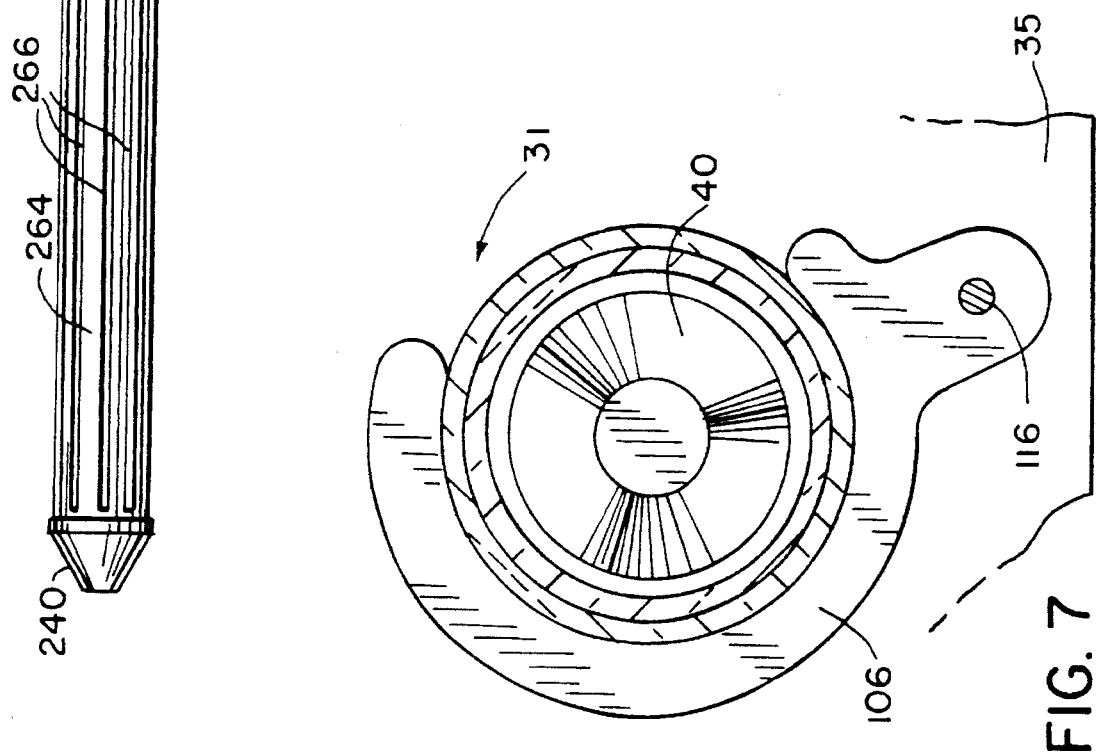

FIG. 8
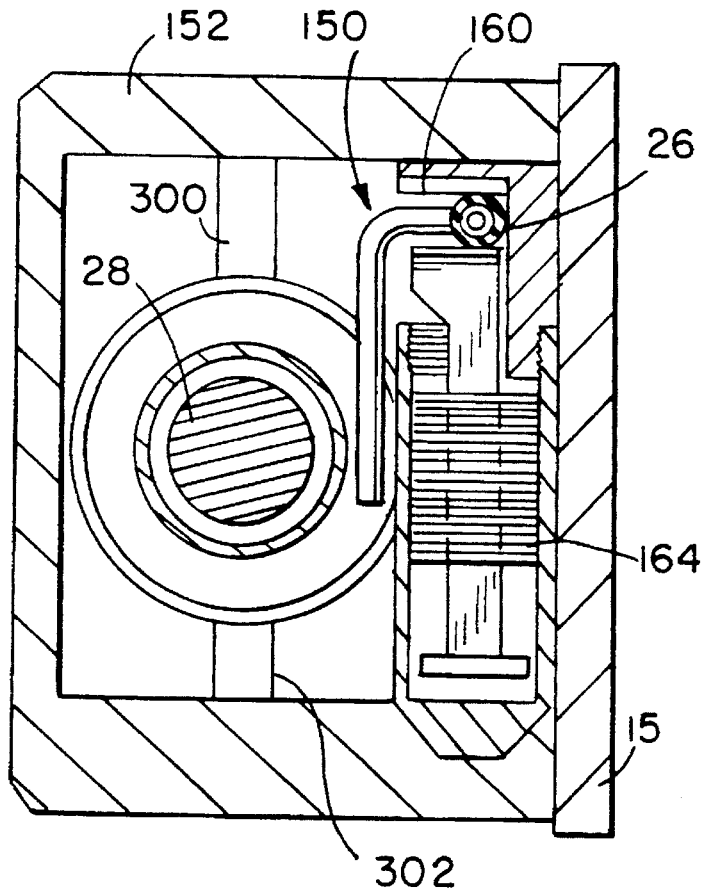
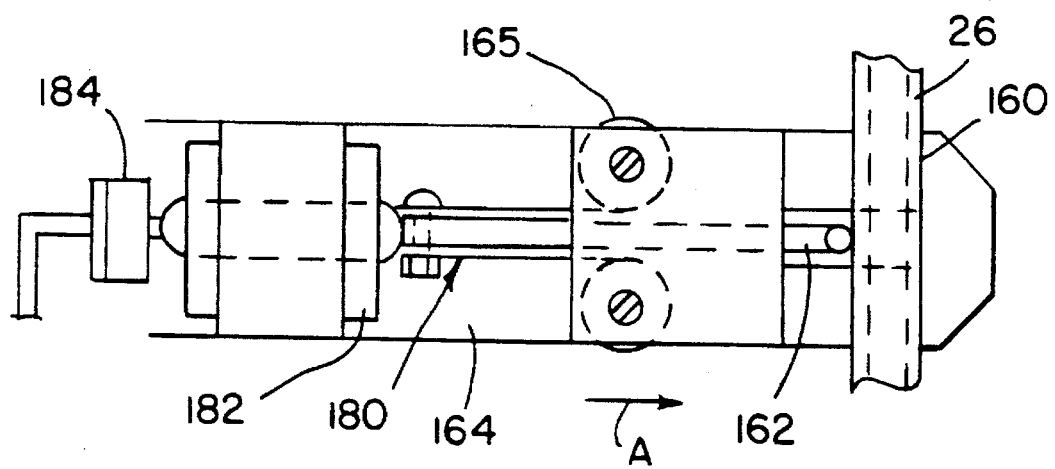
FIG. 9

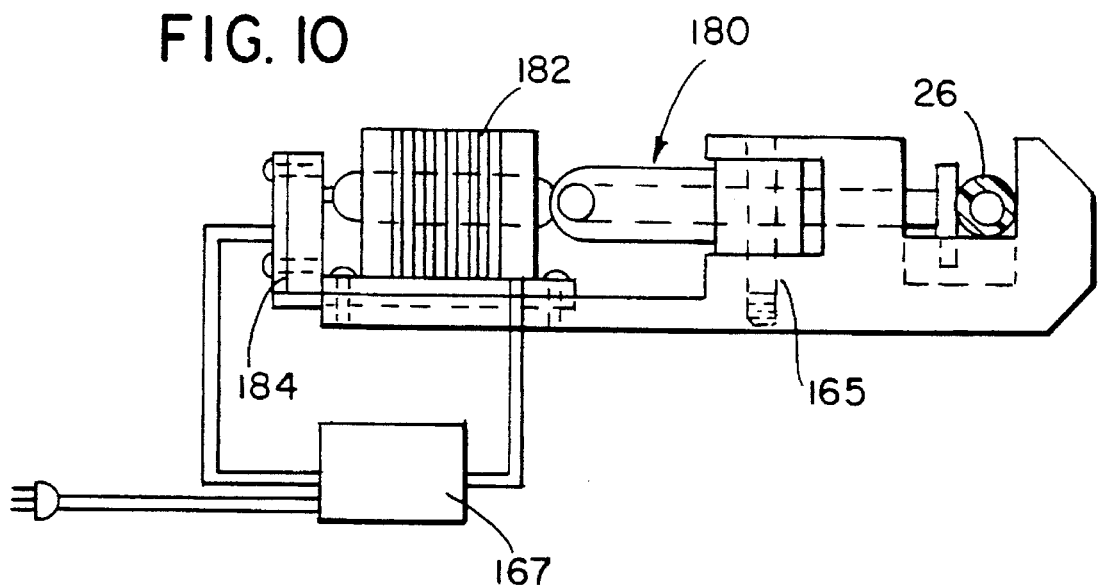
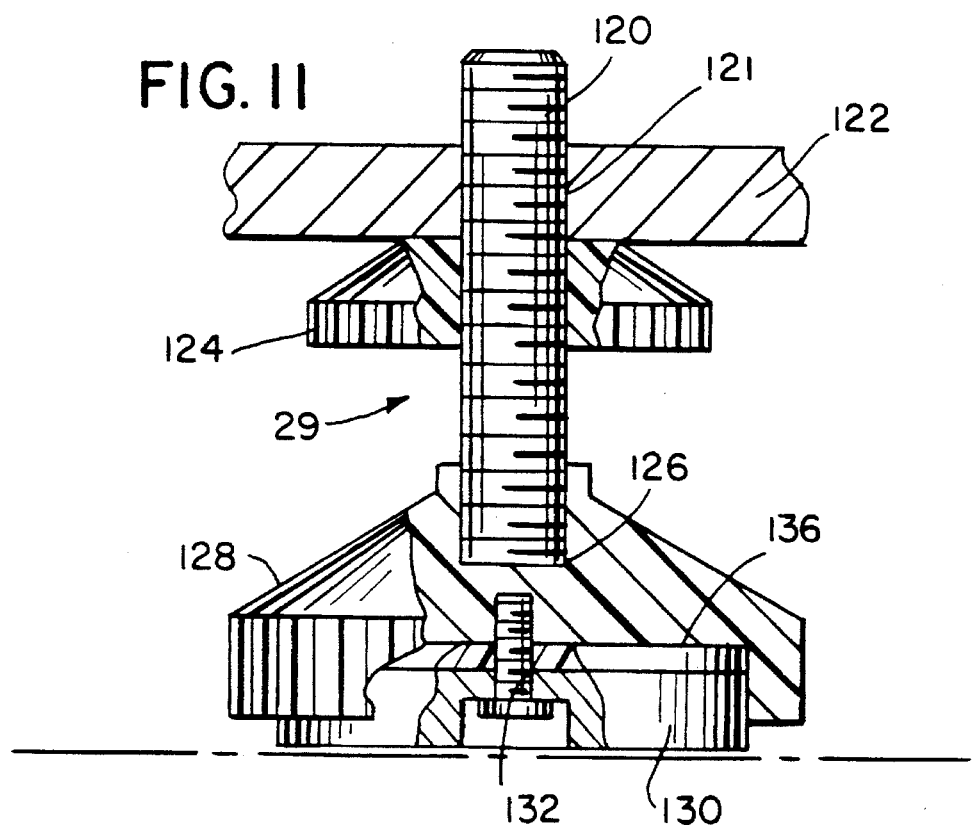

APPARATUS FOR SUPPORTING AND DRIVING A ROTATING CYLINDER

BACKGROUND OF INVENTION

1. Field of Invention

This invention is generally related to a rotating cylinder for treatment of materials and is specifically related to an apparatus for supporting and driving a rotating cylinder such as a cylindrical ultraviolet irradiator for the treatment of fluids.

2. Description of the Prior Art

It is well known to support a hollow cylinder with the axis inclined to permit a loose material or fluid to run through the cylinder along its inner peripheral wall while rotating the cylinder to spread the material over the inner surface in order to create a film. A known example of such an apparatus is an irradiator used for the ultraviolet treatment of blood. An example of a rotating cylindrical irradiator was manufactured by the J. J. Dill Company, Kalamazoo Mich. in the 1950's. In the irradiator there described, blood components are introduced into the upper end of an inclined rotating cylinder and allowed to gravity feed along the inner wall of the cylinder as it is rotated in order to allow the blood to form a thin film on the inner wall as it flows toward the lower discharge end. As the blood moves through the cylinder, it is subjected to an axially mounted ultraviolet lamp for irradiating the fluid flowing through the cylinder.

It has been found that by controlling the exposure of blood constituents to ultraviolet light that various foreign microorganisms in the blood supply can be altered or immobilized. For example, various strains of virus can be inactivated and thereafter used to develop a vaccine which may be injected into the blood supply of an animal in order to create a natural immunity to the virus. Such a method has been used to create influenza and rabies vaccines for a number of years.

Currently, the most prevalent use of irradiators for ultraviolet treatment of blood components is for generating serums from the blood of mammals. In a typical example, mammal or human blood is removed from a subject and the platelets are then centrifuged out of the plasma. The remaining serum or basically non-solid clear component of the blood is irradiated to inactivate any virus that happens to be present. This will also typically kill or immobilize any other microorganisms that may happen to be present in the sample. If the plasma is further fractionated, that is, divided into different fractions, such as, by way of example, fibrinogen, different globulin, and literally hundreds of subcomponents which can be segregated by any of the well known methods of separating plasma, each of the fractions can then also be treated using the same irradiating method.

Prior to the development of a practical method for treating large quantities of blood through cylindrical irradiation, a small sample was placed on a flat plate, such as a specimen slide or a microscope slide, and then exposed to ultraviolet light, or a small portion was allowed to flow through a small diameter, clear quartz tube that had an ultraviolet light on the outside of that tube. This method has been successfully used in a laboratory environment for research screening to verify the response of the various fractions to specific exposures to ultraviolet light.

Prior to the nineteen fifties, and prior to the development of the early mass quantity irradiator, it was impractical to treat blood through irradiation even though many of the benefits were well documented. During World War II, transfusions of blood plasma became commonplace. It was at this time that it became clear through the large scale of available documentation that transfusion of plasma from one person to another caused the spread of certain viral diseases among patients drawing from a common pooled blood plasma source. At this time, it became apparent that large scale irradiation to kill or immobilize these various microorganisms was essential to creating a safe blood plasma supply, with the irradiator as disclosed in the aforementioned patent being the first successful system for irradiating blood plasma on a commercial scale. This was a successful effort greatly increasing the availability of safe blood plasma supplies in the nineteen fifties.

Unfortunately, during the Korean war it appeared that the irradiation treatment was not successful for killing or immobilizing various strains of hepatitis and by 1960 commercial irradiation for human blood plasma pools basically ceased. In 1964, the World Health Organization published a statement that all pooled plasma from blood banks, plasma banks, and producers of plasma, could not be distributed for human transfusion. The commercial use of irradiators diminished to near zero. While certain applications remained viable, particularly for bovine blood plasma, the extremely reduced demand for commercial irradiators resulted in halting the continuing development of the technology.

More recently, irradiation has been found to be particularly successful in the inactivation of rabies virus for the manufacture of rabies vaccine. Of the less than twenty-five known commercial irradiators still in existence in the world the vast majority are used for producing rabies vaccine. On a lesser scale, the irradiators are also effective against and used for influenza virus, and at least one company in Italy and one in Japan, use the irradiator of the aforementioned reference to manufacture influenza vaccine.

Over the last several years, it has been determined that blood fractions irradiation may be a valuable treatment for immobilizing certain viruses and potentially placing the patients so infected in long term remission.

With the renewed interests in ultraviolet treatment of blood constituents, there is a pressing need for an improved, high volume irradiator apparatus. Moreover, the currently available technology, while very successful for its intended purpose over thirty-five years ago, relied very heavily on trial and error and the steady monitoring by experienced technicians. There remains a need for a commercial irradiator which is reliable independently of the high level of skill generally required with past machinery in order to assure that the promising new irradiation treatments can be duplicated on a commercial level.

SUMMARY OF THE INVENTION

The subject invention is directed to a device for supporting and rotating a cylinder of the type used for treating fluids. In the preferred embodiment, the cylinder is hollow and is mounted for rotation about an inclined axis for permitting fluids such as blood constituents to flow by gravity downward along the internal peripheral wall of the cylinder. It is an important aspect of the invention that the angle of inclination, the drive speed and the thickness of the fluid film on the wall of the cylinder are controlled and variable in order to achieve consistent and predictable results during various treatment processes. The various monitoring features are very critical in controlling the precise exposure of the fluid to the lamp. A matrix made up of input fluid flow rate, lamp intensity, film thickness, rotational speed and inclination angle determines the actual exposure process. Accurate information of all variables is essential to a reliable and predictable process.

It is another important feature of the invention that both the drive system and the mounting system are designed to isolate the cylinder from external vibrations and to minimize non-uniformity of the fluid film. In the preferred embodiment of the invention, integral monitoring systems are provided for monitoring and controlling the inclination angle and the rotational speed of the cylinder as well as for monitoring the thickness of the fluid film in order to assure uniform exposure to the light source. A sensor may also be provided to monitor the intensity of the light source.

In one embodiment of the invention, the cylinder is mounted on roller bearings having a resilient bearing surface for isolating potential external vibration. In the preferred form, a removable resilient ring is placed on the outer surface of the bearing roller to provide the isolating surface. The resilient roller bearing configuration may also be used to support the cylinder on the selected angle of inclination. To further isolate the cylinder against vibration, the drive mechanism is mounted on a floating mount with a resilient, sound deadening o-ring drive extending around the outer perimeter of the cylinder.

The base is mounted on unique levelers permitting independent leveling of each of the three or four legs without a tendency of the structure to walk. This is accomplished by utilizing a unique levelling leg assembly having an internal shaft with an outer spin ring. The spin ring is axially adjustable against a stop provided on the base for permitting the base to move relative to the shaft, reducing any tendency of the leg to walk by maintaining it stationary against the support surface.

The lamp mounting system has also been modified from prior art models to provide more accurate placement of the lamp along the axis of the cylinder while at the same time providing means for isolating the lamp assembly from the interior of the cylinder. A unique collection cup is provided at the discharge end of the cylinder for receiving the discharged, treated fluid and the collection cup is designed to receive and seat one end of the lamp assembly. In the preferred embodiment of the invention, the collection cup is mounted in a stationary position in axial alignment with the discharge end of the cylinder. The collection cup comprises an outer cylindrical sleeve with a diametric base. An inner sleeve is provided along the axis and passes through the base for added strength. The collection cup sits in a C-shaped bracket mounted on the cylinder support plate and adapted to swing radially to remove the cup from the assembly for maintenance. The C-clamp is designed to substantially surround and engage the extended inner sleeve of the cup to hold it in axial position relative to the cylinder. The lamp support assembly includes a tapered mounting cap which is adapted to be received in the inner open end of the inner cup sleeve. The taper on the mounting cap permits the lamp assembly to be self seating.

While in the preferred embodiment the cylinder is fully supported by the resilient bearing surfaces, inlet and discharge end caps are provided to isolate the interior of the cylinder and to provide mounting surfaces for supporting the collection cup, the lamp assembly and fluid input conduits. In the preferred embodiment, the open end of the collection cup is received in an annular channel of the discharge end cap and a resilient seal may be provided to seal the end cap. Where desired, a fluid or non-contact seal may be provided between both end caps to hermetically seal the interior of the cylinder. A sensor may be positioned on the inlet end cap to monitor the intensity of the lamp.

Where desired, the base of the support structure may be provided with a splash guard to assure that any spillage is not introduced into the interior of the structure, greatly reducing maintenance and clean up in the event of an accidental spill. Also, the control unit is positioned at a remote location, assuring that the cylinder assembly is isolated to the fullest extent possible. The lamp assembly includes an outer sleeve for completely isolating the lamp from the interior of the cylinder, again facilitating cleanup in the event a shut down results in fluid dripping from the inner cylinder wall onto the axially positioned lamp.

In an alternative embodiment, various other lamp sources may be substituted for providing other types of treatment procedures. For example, a laser lamp may be utilized in the assembly with a minimum of structural modification.

Typically, a stainless steel cylinder is used. However, other materials may be substituted. For example, a quartz cylinder may be used and since quartz transmits ultraviolet light, this permits placement of the light source outside of the cylinder. Also, the use of a quartz cylinder permits the placement of a sensor in the cylinder wall to precisely monitor the thickness of the film in combination with the light intensity.

The inlet tube conduit includes a unique tube pincher to assure prompt stoppage of flow in the event of a shut down due to power failure. The system is designed to be fail safe and is a particularly important feature when the cost of blood specimens is considered. Power is required to permit fluid flow and any loss of power automatically shuts down the flow through the conduit.

The subject invention provides an improved cylinder fluid treatment device that is reliable, substantially fail safe and provides accurate and predictable results. It is particularly useful in the irradiation treatment of blood constituents but is readily adaptable to other rotating cylinder treatment procedures.

In one method of treatment in accordance with the teachings of the subject invention, it has been found that irradiation therapy is successful in impeding the progression of the AIDS virus, potentially placing HIV-positive subjects in long term remission. In experimental tests, it has been found that a psoralen derivative drug attaches itself to white blood cells that have been identified as HIV receptors. By ingesting the psoralen drug, which has a natural biochemical dye, the specific HIV-receptive platelets can be identified. Thereafter, a specimen of the treated blood is removed from the body and fractionated in the normal manner. The plasma and white blood cells are then treated by irradiation and exposed to ultraviolet light. With proper exposure, psoralen dye absorbs the ultraviolet light without damaging or altering the unaffected cells. This damages or alters the HIV-receptor cells without altering the remainder of the blood supply. The blood fractions are then recombined and replaced in the subject's blood supply. Experimental results have indicated that as the blood comes back into the subject's blood stream, the body recognizes that there is a foreign substance, which is the altered receptor cells, and develops an antibody to attack these cells. It has been found that the antibody is active against all HIV receptor-type cells, not just the specimens which have been altered by ultraviolet treatment. Basically, the end result is that the antibody starts destroying all the receptor white blood cells to which the HIV virus would attach. These blood cells are rendered immobile and it appears the HIV virus cannot multiply without the presence of viable receptor cells. While this does not eliminate the presence of the HIV virus in the subject, it shows promising indications of an ability to place the subject in long term remission. Further, it appears that upon recurrence of the receptor cells in the body, the process can be repeated with similar results. While experiments have been promising, at the present time the various potential side effects have not been determined and large scale clinical testing will be necessary. Similar tests are underway for treatment of certain cancers and various other blood related diseases.

The various features and aspects of the invention are more clearly described in the accompanying drawings and detailed description of the preferred embodiments which follow.

BRIEF DESCRIPTION OF THE DRAWINGS

FIG. 7 is a cross-sectional view taken generally along the line 7—7 of FIG. 3.

FIG. 8 is a cross-sectional view looking generally along the line 8—8 of FIG. 3, and diagrammatically showing the location and detail of the sensors and the tube pincher of the irradiator of FIG. 1.

FIG. 9 is a detailed top view of the tube pincher, with the cover removed.

FIG. 10 is a side view of the tube pincher shown in FIG. 9, with the cover removed.

FIG. 11 is an enlarged view, partially in section, showing the leveler assembly of the subject invention.

FIG. 12 is a perspective view of an alternative embodiment of the lamp assembly.

DETAILED DESCRIPTION OF THE PREFERRED EMBODIMENTS

Figure 1:
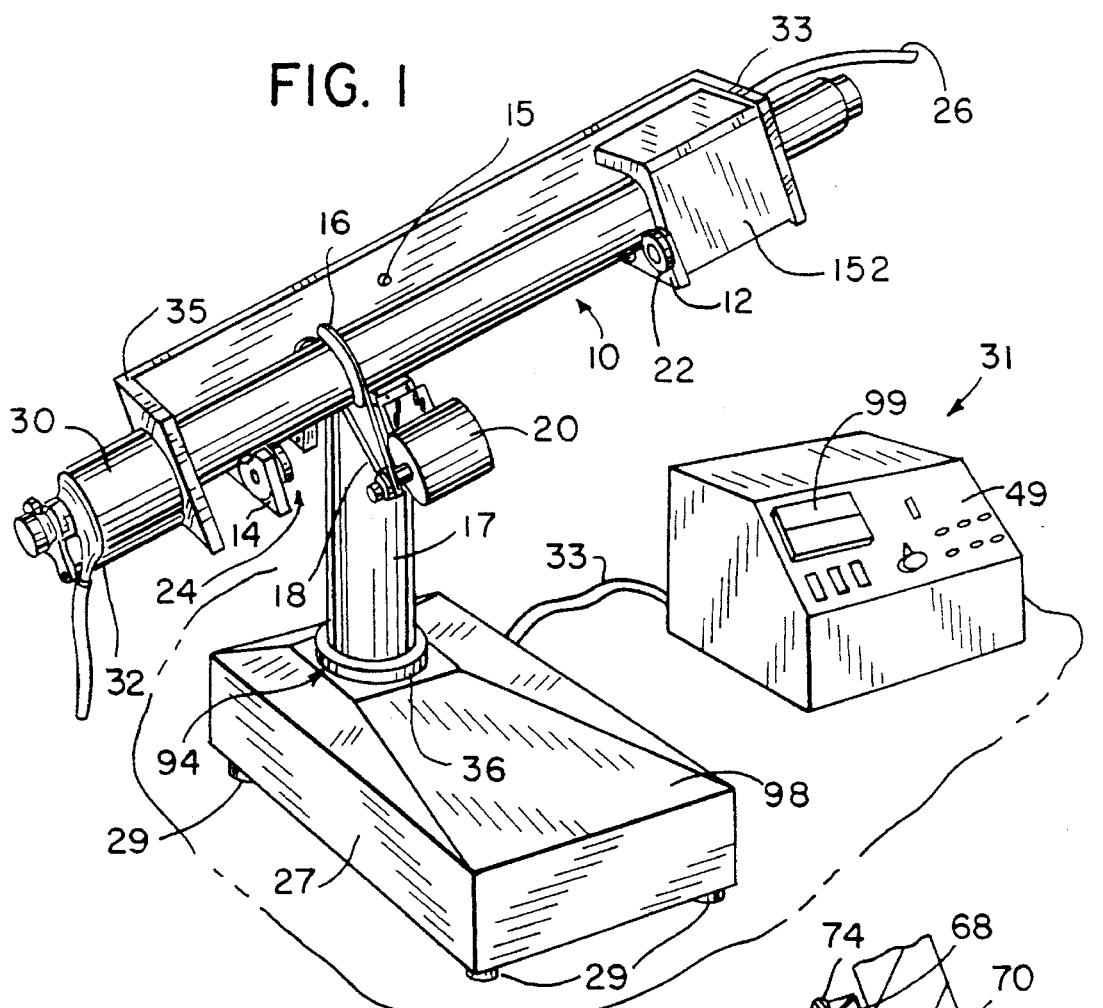
FIG. 1 is a perspective view of the irradiator assembly of the subject invention.
Figure 2:
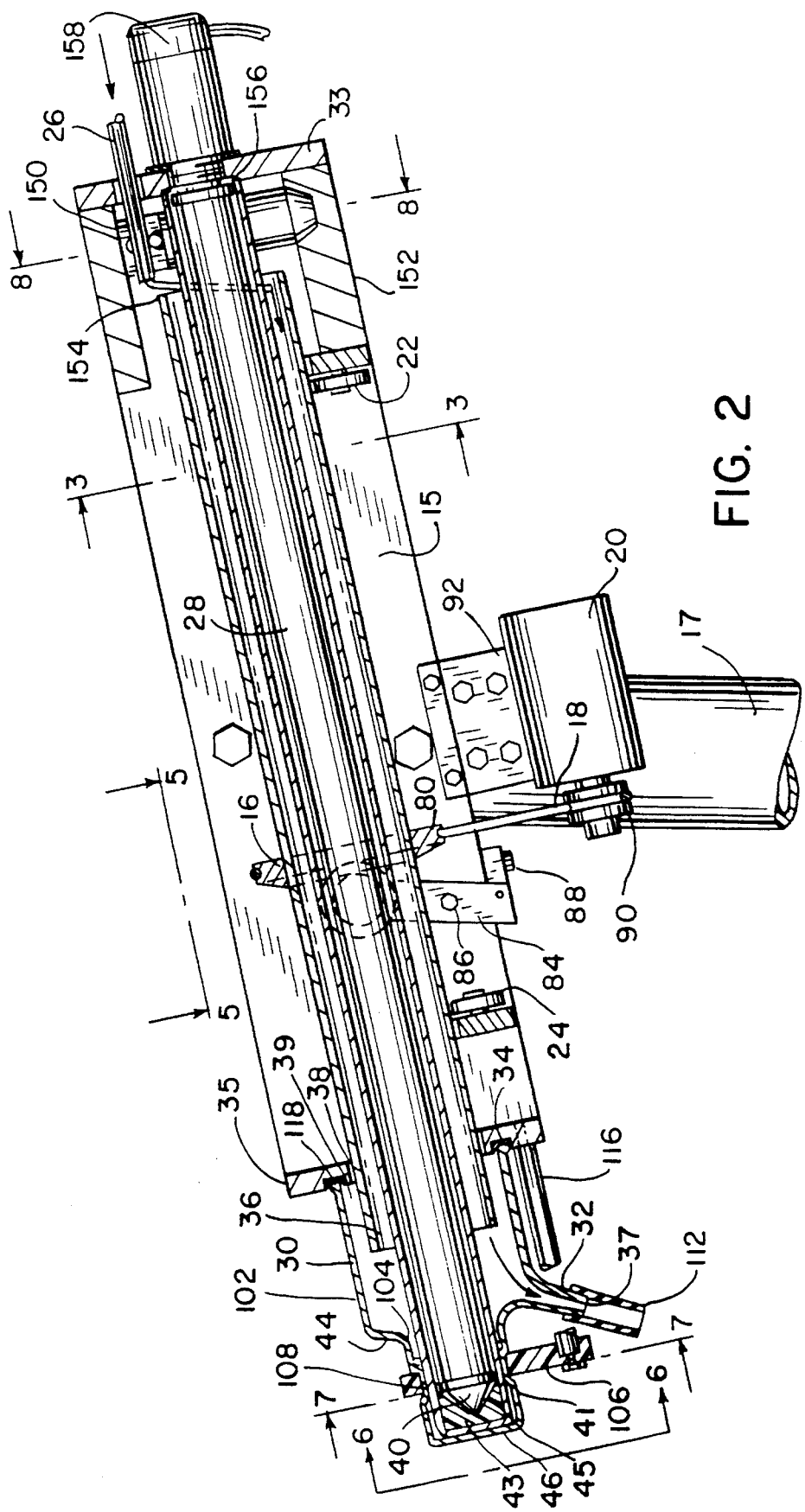
FIG. 2 is a fragmentary cross-sectional view along the axis of the cylinder, showing the detail of the assembly of FIG. 1.

As best shown in FIGS. 1 and 2, the irradiator of the preferred embodiment consists of an inclined cylinder 10 mounted for rotation on a pair of support members or brackets 12 or 14, which are mounted on and extend outwardly from a support plate 15. The support plate 15 is mounted on a support column 17, and may be indexed relative thereto to change the angle of inclination of the support plate and the rotating cylinder 10. A drive ring 16 circumscribes the cylinder 10, and a drive belt 18 is in position in the drive channel in the ring 16. The drive belt is driven by a motor 20 to rotate the cylinder about its axis and relative to the support brackets 12 and 14. Bearings 22, 23, 24 and a fourth bearing (not shown) (see FIG. 2) are provided in the brackets 12 and 14, respectively, for supporting the cylinder to permit it to rotate freely in response to the motor 20.

In the preferred embodiment, the support column 17 is secured to a base 27, which includes a plurality of leveler legs 29, whereby the entire assembly may be leveled for proper orientation. The leveler legs of the preferred embodiment are better illustrated in FIG. 10 and are described in detail herein. A remote power supply/control panel assembly 31 is cabled to the irradiator unit via cable 33, for supplying power to the unit and for monitoring the various parameters controlling the process.

The irradiator is used to expose selected constituents of human blood to various stimuli such as ultraviolet light, laser treatment, or the like. To that end, a supply tube 26 is provided at the upper end plate 33 of the support plate 15, and is attached to a supply of blood. The blood flows through the tube 26 and is introduced onto the interior peripheral surface 11 (FIG. 3) of the cylinder 10. As the cylinder slowly rotates, the blood forms a liquid film over the entire surface of the cylinder.

Figure 3:
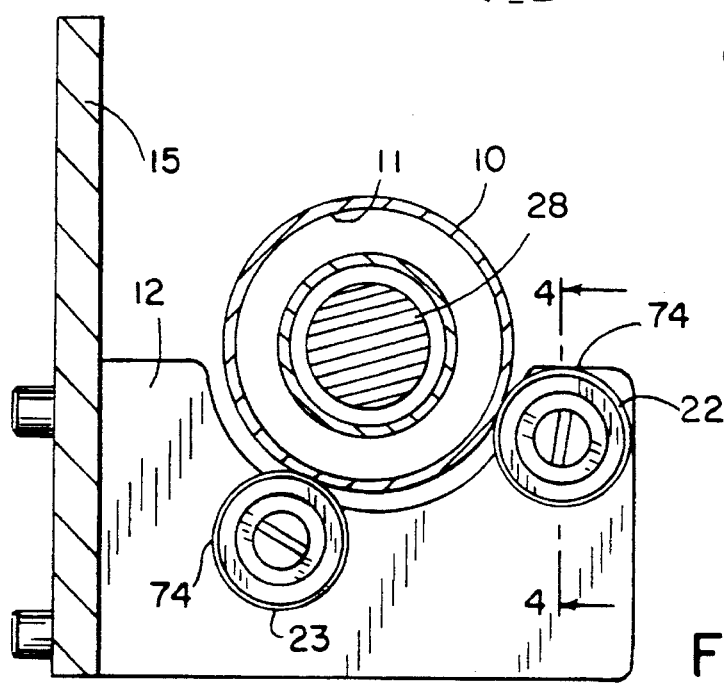
FIG. 3 is a cross-sectional view taken along the line 3—3 of FIG. 2 and through the axis of the cylinder, showing the bearing mounting supports for supporting the cylinder for rotation.

In the preferred embodiment, and as better seen in FIGS. 2 and 3, an ultraviolet lamp assembly 28 is positioned along the axis of the cylinder and is operable to expose the blood in the cylinder to ultraviolet rays for treatment purposes.

The blood is released into a collection cup 30 at the opposite end of the cylinder and is released through an exit nipple 32 at orifice 37. In the preferred embodiment, the collection cup 30 has an open mouth 39 (FIG. 2) which is received in a recessed channel 34 provided in the lower end plate 35 attached to the support plate 15. The recessed channel 34 forms an annulus around the through hole 38. The lower or exit end 36 of the cylinder 10 passes through the through hole 38 and into the open mouth of the cup, but does not come in contact with the cup at any point.

The lamp assembly 28 is supported by the upper end plate 33 attached to the main support plate 15 and by the collection cup which is mounted in the recess in the lower end plate 35. While the lamp extends the length of the cylinder, it is not in contact with it at any point, and the cylinder is free to rotate relative to the lamp.

In the preferred embodiment, the lower end 40 of the ultraviolet lamp assembly is axially supported by a reduced cylindrical member 41 of the collection cup 30 (see FIGS. 2 and 7). As best seen in FIG. 2, the cup 30 is preferably a glass cup with an open mouth 39 and a closed bottom 44. The reduced cylindrical portion 41 extends outwardly from the bottom 44 and has a hollow cylindrical interior which is large enough to accommodate the outer perimeter of the lamp 28. In the preferred embodiment a mounting block 43, with a tapered bore or receptive socket 45 is positioned in the closed end 46 of the reduced collection cup. The conically tapered lower end cap 40 of the lamp assembly is received in the bore or socket, whereby the lamp is self-centering in the collection cup assembly.

In the preferred embodiment of the invention, the support plate 15, and thus the cylinder, lamp and collection cup assembly, may be tilted relative to the column 17 to alter the inclined angle of the cylinder and thereby control the rate of gravity feed of the blood film along the cylinder, controlling the time duration of exposure to the lamp. The thickness of the film is controlled by the rotational speed of the cylinder as driven by the motor 20. The control module 31 includes a face control panel 49 for controlling the various parameters of the entire system.

In the preferred embodiment of the invention the control module 31 is remote from the base 27 and the irradiator assembly. This permits the irradiator to be completely isolated from human contact during operation.

The drive ring 16, support bearings 22, 23, 24 and a fourth bearing (not shown) and the drive bearing 52 (FIGS. 2 and 5) have been significantly modified over the prior art to provide for smoother rotation of the cylinder to assure uniform thickness of the film in the cylinder and to assure uniform feed in order to optimize the exposure of the blood to the lamp in a controlled process.

Figure 4:
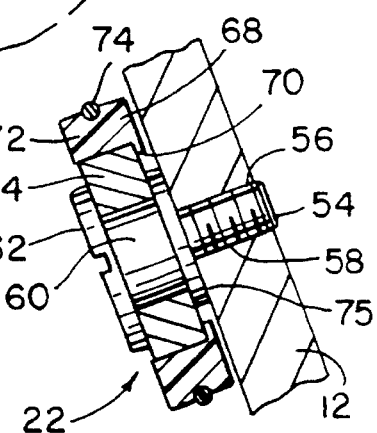
FIG. 4 is a cross-sectional view taken generally along the line 4—4 of FIG. 3.
Figure 5:
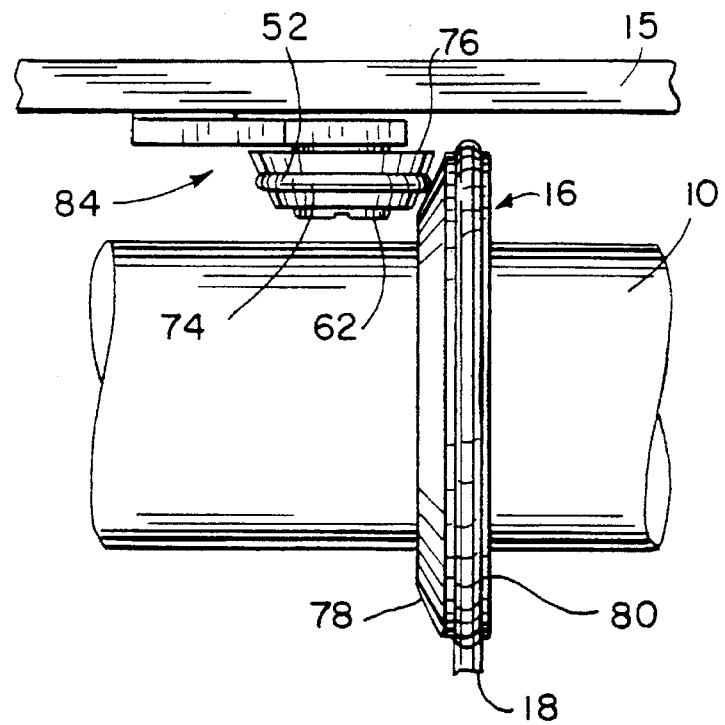
FIG. 5 is a view looking generally along the line 5—5 of FIG. 2.
Figure 6:
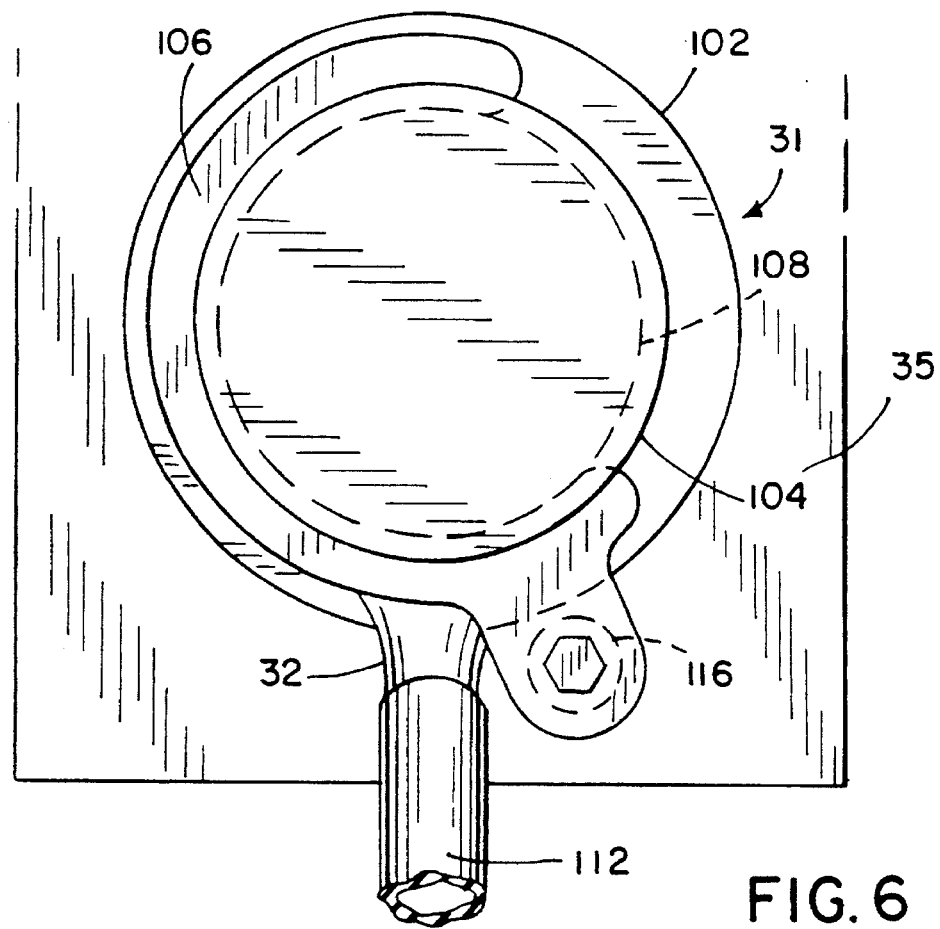
FIG. 6 is a view looking generally along the line 6—6 of FIG. 2.

The improved bearing assembly is best shown in FIGS. 3, 4 and 5. Specifically, FIG. 4 shows a sectional view of the bearing 22 mounted on support bracket 12 for supporting the cylinder 10 (FIG. 3). The bearing assembly 22, and each of the remaining bearing assemblies 23, 24, and a fourth bearing (not shown) and 52, are mounted on bearing shaft or stud 54 directly on the respective support bracket. The bearing shaft has a reduced, threaded outer end 56 adapted to be received in a threaded or tapped hole 58 in the support bracket. An enlarged shoulder defines a bearing race 60 which is in axial alignment with the threaded end 56, and an enlarged slotted head 62 is provided outboard of the bearing race to secure the bearing assembly on the bearing race. Typically, and in the manner well known to those skilled in the art, the bearing assembly is positioned on the race externally of a plurality of ball-bearing elements to provide smooth rotation of the roller bearing relative to the roller race. Typically, the ball-bearing elements of the type encased in a circular carrier or cage 64 are positioned directly on the bearing race. The roller 68 is then mounted directly on the bearing cage 64 for rotation therewith, with the internal ring 70 positioned against the relief face of the bearing cage 64 to hold the roller 68 in position and keep it out of contact with the internal face of the slotted head 62. An annular groove 72 is provided around the outer periphery of the roller 68. A resilient, replaceable O-ring 74 is placed in the groove. This assures that the only contact of the cylinder 10 is with the resilient O-ring 74, providing a good dampening between the cylinder and the rest of the assembly (see FIGS. 3 and 5). A spacer washer 75 is provided to assure clearance between the support bracket and the bearing race.

The thrust bearing assembly 52 for engaging the drive ring 16 is essentially same as that just described with the exception that the outer surface 76 of the bearing roller is tapered, as best shown FIG. 5. This ensures proper clearance between the tapered face 78 of the drive ring 16 and the roller bearing assembly 52.

The drive train including the improved drive ring 16 and thrust bearing assembly 52 is best shown in FIG. 5. The drive ring 16 is mounted in a manner to circumscribe the cylinder 10. The drive ring of the preferred embodiment includes two important features which may be used independently or in combination with additional features of the invention. The bearing face 78 of the drive ring 16 is at an oblique angle relative to the axis of the cylinder. This permits the support bearing 52 to bear directly against the drive ring. This is important since in the preferred embodiment this bearing is the only element utilized to keep the cylinder from sliding along its axis when the cylinder is at an inclined angle to permit gravity feed of fluids. Specifically, by providing a drive ring adapted for receiving a bearing support, it permits the cylinder to be floating only on the roller bearings 22, 23, 24, and a fourth bearing (not shown) and 52, providing for the smooth operation essential to maintaining a uniform film thickness for predictable and controlled exposure conditions.

The drive ring 16 also includes an annular channel 80, which in the preferred embodiment is a concave arcuate groove adapted for receiving a drive belt 18 of circular cross-section such as by way of example, an O-ring. This provides a smooth drive system assuring uniform rotational speed of the cylinder 10.

The thrust bearing support bracket assembly 84 is essentially "L"-shaped and is pivotal about the center of the "L" at pivot point 86 (FIG. 2). The bracket is secured directly to the support plate 15 via a fastener such as the adjustment stop bolt 88. The bracket can be pivoted about point 86 in order to precisely align the drive ring 16 with the drive pulley 90 of the drive motor 20, and then locked in position in a manner well known to those who are skilled in the art. The hinged motor assembly 20 is mounted on a mounting bracket 92 which is secured directly to the support plate 15.

As shown in FIG. 1, the support column 17 is inserted in a receptive opening 94 in the base 27 and a protective ring flange 96 is provided around the support column to assure that material does not fall down into the base in case of a leak or spillage. In addition, it will be noted that the preferred embodiment of the base includes a cover 98 with tapered or angled sides to assure that any spillage runs away from the column rather than toward it and into the opening 94.

The collection cup 31 is generally shown in FIGS. 1, 2, 6 and 7. In the preferred embodiment, the collection cup is made of blown clear glass or other suitable material and includes an outer cup 102 and an integral inner cup 104. While the preferred embodiment of the cup is of an integral construction, this is not necessary to meet the objectives of the invention. The integral inner cup 104 is primarily used for supporting the lower end 40 of the lamp assembly. The circular or C-shaped cup support 106 is adapted to engage the inner cup 104 to support the cup in the assembly. Specifically, a recessed channel 108 (FIG. 2) may be provided to receive and seat the support 106. In the preferred embodiment, the C-shaped support 106 is pivotally mounted on a rod 116 which is secured to the end plate 35 of the support 15 (see FIG. 2). In order to place the cup in the assembly, the support 106 is swung out of the way and the open mouth of the cup 31 is placed in the receptive channel 34 in the end plate 35. After the cup is properly positioned, the support 106 is pivoted into support position, engaging the receptive channel 108 in the inner cup 104 of the cup 31. This assembly permits quick release of the cup for cleaning and maintenance purposes. Where desired, a resilient gasket 118 may be provided between the lip of the open end of the cup and the plate 35 to seal the interior of the cup relative to external elements. The exit nipple 32 is provided for releasing collected fluids from the irradiator assembly. Typically, the exit nipple is attached to a flexible tube or conduit 112 in the well known manner.

The remote control module 31 and control panel 49 are also shown in FIG. 1. All controls for the irradiator operation are housed in this module. The control panel includes a readout module such as an LED readout 99 or the like to provide visual monitoring of the light intensity, speed of rotation of the cylinder, flow rate of the fluids and other parameters controlling the irradiation process. The control box is connected to the irradiator assembly via cable 33 which enters the rear of the support base 27.

FIG. 11 illustrates an enlarged view of one of the leveler legs 29 for the support base 27 and, where desired, the control module 31. As there shown, each leveler leg includes a threaded stud 120 which is received in a complementary tapped hole 121 in the bottom wall 122 of the base or module. A jam nut 124 is threadably received on the shaft and is positioned beneath the wall 122. The stud terminates at its lower end 126 in and adjustment wheel 128. In the preferred embodiment, the adjustment wheel is permanently secured to the shaft in order to ensure that the wheel and shaft always move together. The wheel is rotatably mounted on a base 130, as by threaded pin 132. The shaft 120 and wheel 128 are thus rotatable relative to the base 130. In the preferred embodiment, the wheel 128 includes a circumferential apron to conceal the base 130 for aesthetic purposes.

In operation, rotation of the wheel and shaft will change the relative position of the wall 122 and the base 130. However, the base will not rotate or creep but will stay in a fixed position. Once the wall 122 is properly positioned, the jam nut 124 is tightened against the wall to lock the assembly in place. In the preferred embodiment, a teflon or graphite washer 136 may be positioned between the base 130 and the wheel 128 to reduce friction. Preferably, the base is made of a high density rubber or polyurethane. This configuration provides a leveler assembly which allows leveling of the various elements without rotating the base of the leveler, assuring that it is non-skid and non-marring.

The irradiator of the present invention also includes an improved and novel tube pincher 150, as specifically shown in FIGS. 8, 9 and 10. With specific reference to FIG. 8, the tube pincher is communication with the inlet tube 26 and is designed to pinch the tube in the event there is a power failure or shut-down of the system. The plunger 150 remains open by virtue of electrical current flowing through the solenoid coil 166. As shown in FIGS. 2 and 8, the tube pincher can be mounted on the support plate 15 of the assembly, and within the U-shaped cover 152 (FIG. 1). Also, note that the upper inlet end 154 of the cylinder 10 is within the cover 152 and that the upper end 156 of the lamp assembly 28 extends through the cover 152 and is secured on the upper end support plate 33. The power supply for the lamp is remote and connected at 158 via cable 159.

The tube pincher, as shown diagrammatically in FIG. 8, and in detail in FIGS. 9 and 10, includes a channel 160 in which the tube 26 is placed and secured. A plunger mechanism 162 is in communication with the channel and is designed to advance in the direction of arrow A (FIG. 9) and into engagement with the tube in response to a control signal. The control mechanism for operating the pincher is housed in the housing 164 and is better shown in detail in FIG. 9. In the preferred embodiment, the tube pincher is designed to be in the open position, as drawn, whenever the irradiator is operable. In the event of a shut-down or a power failure present at module 31, and a loss of power signal is present at the pincher control mechanism 167, the coil spring 180 mounted on housing 164, as at 165 closes the plunger in the direction of arrow A to shut off the flow in tube 26. In the preferred embodiment, the tube pincher includes a plunger 162 which is normally closed against the tube 26 by a biasing element such as the spring 180. In its preferred form, the spring is a linear tension spring adapted for exerting a constant force on the plunger regardless of its position. The plunger is mounted on a solenoid actuator 182 which is controlled by a micro switch 184. Whenever the irradiator system is in an operative mode, the solenoid is actuated to act against the spring 180 and retract the plunger, for opening the tube 26 and allowing flow therethrough. Thus, the unique tube pincher of the subject invention is operative to close the supply tube 26 whenever the system is shut down for any reason.

An alternative lamp assembly is shown in FIG. 12. This configuration includes a sealed lamp unit 228 having a tapered tip end 240 which is adapted to be received in the receptive socket 45 of the collection cup 30 (see FIG. 2). The opposite end 256 is adapted to be inserted through the upper end plate 33 of the support assembly (see FIG. 2), with the power cable or fiber optic light guide 258 being coupled to a remote power supply 260. In the preferred embodiment, the lamp 228 may include a slotted cover 264 having a plurality of elongated through slits 266 through which the light passes. This configuration is particularly useful for laser processing techniques.

One of the important features of the irradiator system of the present invention is the provision of sensors 300, 302 in the system, see FIG. 8, to determine the intensity of the ultraviolet light and the thickness of the film to monitor actual exposure of blood sample to the irradiating light source. The sensors for sensing the intensity of the ultraviolet light are placed in the upper end of the cylinder 10 and are mounted on the stationary upper end bracket 152, extending into the cylinder between the outer peripheral wall of the cylinder and its axis, with the sensor mechanism aimed in the cylinder toward the light source 28. A similar sensor may be provided in the opposite direction for monitoring reflective light in order to determine the thickness of the film.

In addition, an alternative embodiment for the sensor should be provided showing the sensor on the external surface of the cylinder. This is particularly useful when the cylinder is made of an ultraviolet transmitting material such as quartz, where the intensity of the light source can be measured at the first mentioned sensor and the relative of the intensity of the light source can be measured at the external sensor, to thereby determine the thickness of the film.

In operation, the cylinder 10 is mounted for rotation about an inclined axis for permitting fluids such as blood constituents to flow from tube 26 onto the inner wall 11 of the cylinder and by gravity downward along the internal peripheral wall of the cylinder and into the collection cup 30, where it is collected and discharged through the orifice 37 of nipple 32 and into the collection tubing 112. The lamp is energized to expose the film of fluid throughout the length of the cylinder. It is an important aspect of the invention that the angle of inclination, the drive speed and the thickness of the fluid film on the wall of the cylinder are controlled and variable in order to achieve consistent and predictable results during various treatment processes. The various monitoring features are very critical in controlling the precise exposure of the fluid to the lamp. A matrix made up of input fluid flow rate, lamp intensity, film thickness, rotational speed and inclination angle determines the actual exposure process. Accurate information of all variables is essential to a reliable and predictable process.

In one such process, it has been found that ultraviolet exposure may have an important and positive effect in impeding the growth of the HIV virus in human subjects. In experimental tests, it has been found that a psoralen derivative drug attaches itself to white blood cells that have been identified as HIV receptors. By ingesting the psoralen drug, which has a natural biochemical dye, the specific HIV-receptive platelets can be identified. Thereafter, a specimen of the treated blood is removed from the body and fractionated in the normal manner. The plasma and white blood cells are then treated by irradiation and exposed to ultraviolet light. With proper exposure, psoralen dye absorbs the ultraviolet light without damaging or altering the unaffected cells. This damages or alters the HIV-receptor cells without altering the remainder of the blood supply. The blood fractions are then recombined and replaced in the subject's blood supply. Experimental results have indicated that as the blood comes back into the subject's blood stream, the body recognizes that there is a foreign substance, which is the altered receptor cells, and develops an antibody to attack these cells. It has been found that the antibody is active against all HIV receptor-specific cells, not just the specimens which have been altered by ultraviolet treatment. Basically, the end result is that the antibody starts destroying all the receptor white blood cells to which the HIV virus would attach. These blood cells are rendered immobile and it appears the HIV virus cannot multiply without the presence of viable receptor cells. While this does not eliminate the presence of the HIV virus in the subject, it shows promising indications of an ability to place the subject in long term remission. Further, it appears that upon recurrence of the receptor cells in the body, the process can be repeated with similar results. While experiments have been promising, at the present time the various potential side effects have not been determined and large scale clinical testing will be necessary. Similar tests are underway for treatment of certain cancers and various other blood related diseases.

Typically, a stainless steel cylinder is used. However, other materials may be substituted. For example, a quartz cylinder may be used and since quartz transmits ultraviolet light, this permits placement of the light source outside of the cylinder. Also, the use of a quartz cylinder permits the placement of a sensor in the cylinder wall to precisely monitor the thickness of the film in combination with the light intensity.

While certain features and embodiments have been described in detail herein, it will be understood that the present invention encompasses all of the enhancements and modifications within the scope of the following claims.

What is claimed is:

1. An apparatus for processing material by axially rotating a hollow cylinder, wherein the material is introduced into the hollow cylinder, the apparatus comprising:
   a. a cylinder having an outer peripheral wall, an inner peripheral wall and an axis at an inclined angle, the cylinder further including an upper inlet end and a lower discharge end;
   b. a support plate having a lower end plate extending therefrom, the lower end plate positioned substantially perpendicular to the cylinder axis, and having an axial through hole larger than the cylinder the through hole adapted for coaxially receiving the lower discharge end of the cylinder;
   c. a support member attached to the support plate, the support member disposed for supporting the cylinder while permitting axial rotation of the cylinder;
   d. a collection cup attached to the lower end plate, the collection cup comprising an outer cylindrical sleeve having an open end and an opposite closed end, the open end adapted to be mounted over the through hole of the lower end plate; and
   e. the collection cup including an inner sleeve coaxial with the outer sleeve and having one end extending through the closed end of the cup to form an extension and an opposite open end in communication with the cylinder.

2. The apparatus of claim 1, further including a support for holding the collection cup in place relative to the cylinder, the support adapted for surrounding the extension for positioning the cup relative to the axis of the cylinder.

3. The apparatus of claim 2 wherein the collection cup is mounted on the axis of the cylinder.

4. The apparatus of claim 2, wherein the cylinder is mounted for rotation independently of the collection cup.

5. The apparatus of claim 2, wherein the collection cup support further includes a substantially C-shaped bracket pivotally mounted such that the C swings into and out of circumscribing relationship with the extension.

6. The apparatus of claim 1 further including a lamp assembly having an end cap which is adapted to be placed in the open end of the inner sleeve of the collection cup for mounting the lamp assembly in the cylinder.

7. The apparatus of claim 6, wherein the end cap is tapered in the form of a truncated cone and is self seating in the open end of the inner sleeve.

8. The apparatus of claim 6, further comprising an upper end plate extending from the support plate and positioned substantially perpendicular to said cylinder axis in non-contacting relationship with the upper end of the cylinder and spaced outwardly from the upper end of the cylinder, wherein the lamp assembly is elongated and when mounted, extends along the axis of the cylinder, the lamp assembly having an upper end member adapted to be received by the upper end plate.

9. The apparatus of claim 1, wherein:
   a. the lower end plate includes a recessed opening for receiving the open end of the collection cup; and
   b. the open end of the collection cup is shaped to be snugly received in the recessed opening.

10. The apparatus of claim 9, further including a resilient gasket between the open end of the collection cup and the recessed opening in the end plate.

11. The apparatus of claim 1, further comprising, a speed sensor in communication with the outer peripheral wall for monitoring the speed of rotation of the cylinder, and a process sensor in communication with the interior of the cylinder.

12. The apparatus of claim 11, further including an ultraviolet lamp in the interior of the cylinder, and wherein the process sensor monitors the intensity of the ultraviolet light.

13. The apparatus of claim 11 including a lamp assembly positioned outside and adjacent the outer peripheral wall of the cylinder.

14. A fluid treatment apparatus comprising:
   a. a hollow cylinder with an outer peripheral wall, an inner peripheral wall and an axis at an inclined angle, the cylinder further including an upper inlet end for receiving a liquid to be processed and a lower discharge end;
   b. a plurality of bearing elements in engagement with the outer peripheral wall of the cylinder and adapted for supporting the cylinder on a selected inclined angle, the bearing elements having a resilient hearing surface in direct contact with the outer peripheral wall of the cylinder;
   c. a radial ring mounted on the cylinder and projecting radially outwardly therefrom, one of said bearing elements in engagement with the ring for securing the cylinder against axial movement; and
   d. a drive belt circumscribing the outer wall of the cylinder and in communication with a drive means for rotating the cylinder about its axis;
   e. a lower end plate mounted in non-contacting relationship with the lower discharge end of the cylinder and in axial alignment therewith, the lower end plate having an axial through hole larger than the cylinder and adapted for receiving the lower discharge end thereof;
   f. a circumferential channel in the lower end plate and surrounding the through hole thereof;
   g. a collection cup seated in the circumferential channel of the lower end plate, the collection cup comprising an outer cylindrical sleeve having an open end and an opposite closed end, the open end adapted to be seated in the circumferential channel of the lower end plate;

the collection cup including an inner sleeve coaxial with the outer sleeve and having one end extending through the closed end of the cup to form an extension and an opposite open end in communication with the cylinder; and i. a source of light in close proximity to the cylinder for exposing the liquid within the cylinder to the light.

15. The apparatus of claim 14, further including an upper end plate positioned substantially perpendicular to said cylinder axis in non-contacting relationship with the upper end of the cylinder and spaced outwardly from the upper end of the cylinder; and the source of light is a lamp assembly in the hollow cylinder and mounted on the axis thereof, the lamp assembly including:

a. an upper end member adapted to be received by the upper end plated; and b. a lower end cap which is adapted to be placed in the open end of the inner sleeve of the collection cup for mounting the lamp assembly in the cylinder.

16. The apparatus of claim 15, the lamp assembly further including:

a. a light source located along the axis of the cylinder and mounted such that the cylinder rotates independently of the light source; and b. a shield for shielding the light source from the liquid in the cylinder.

17. The apparatus of claim 14, wherein the liquid is a blood constituent and the source of light is, a source of ultraviolet light for irradiating the exposed blood constituent.

18. The apparatus of claim 14, wherein the source of light is a laser lamp located within the cylinder.

19. The apparatus of claim 18, wherein the laser lamp is a self-contained, sealed unit positioned within the cylinder.

20. The apparatus of claim 14, further including:

a. a speed sensor in communication with the outer peripheral wall for monitoring the speed of rotation of the cylinder;

b. a process sensor in communication with the interior of the cylinder.

21. The apparatus of claim 20, wherein the cylinder is of a quartz material adapted for transmitting ultraviolet light therethrough.

22. An irradiator apparatus comprising:

a. a hollow cylinder with an outer peripheral wall, an inner peripheral wall and an axis at an inclined angle, the cylinder further including an upper end and a lower discharge end;

b. a source of ultraviolet light in close proximity to the cylinder for exposing blood constituents within the cylinder to ultraviolet light;

c. a plurality of bearing elements in engagement with the outer peripheral wall of the cylinder and adapted for supporting the cylinder on a selected inclined angle, the bearing elements having a resilient bearing surface in direct contact with the outer peripheral wall of the cylinder;

d. a radial ring mounted on the cylinder and projecting radially outwardly therefrom, one of said bearing elements in engagement with the ring for securing the cylinder against axial movement;

e. a drive belt circumscribing the outer wall of the cylinder and in communication with a drive means for rotating the cylinder about its axis; and f. a control module positioned at a location remote from the irradiator cylinder, with cables for interfacing the control module with the drive means;

g. a lower end plate positioned substantially perpendicular to the cylinder axis, and having an axial through hole larger than the cylinder, the through hole adapted for coaxially receiving the lower discharge end of the cylinder;

h. a circumferential channel in the lower end plate and surrounding the through hole thereof;

i. a collection cup seated in the circumferential channel of the lower end plate, the collection cup comprising an outer cylindrical sleeve having an open end and an opposite closed end, the open end adapted to be seated in the circumferential channel of the lower end plate; and j. the collection cup including an inner sleeve coaxial with the outer sleeve and having one end extending through the closed end of the cup to form an extension and an opposite open end in communication with the cylinder.

* * * * *